United States Patent [19]

Noiles

[11] Patent Number: 4,846,839

[45] Date of Patent: Jul. 11, 1989

[54] APPARATUS FOR AFFIXING A PROSTHESIS TO BONE

[75] Inventor: Douglas G. Noiles, New Canaan, Conn.

[73] Assignee: Joint Medical Products Corporation, Stamford, Conn.

[21] Appl. No.: 179,424

[22] Filed: Apr. 8, 1988

Related U.S. Application Data

[63] Continuation of Ser. No. 11,547, Feb. 6, 1987, abandoned, which is a continuation of Ser. No. 862,023, May 12, 1986, abandoned, which is a continuation of Ser. No. 696,270, Jan. 30, 1985, abandoned, which is a continuation of Ser. No. 578,351, Feb. 9, 1984, abandoned.

[51] Int. Cl.$^4$ .............................................. A61F 2/28
[52] U.S. Cl. ..................................................... 623/18
[58] Field of Search ................... 623/16, 18, 20, 22, 623/23; 433/179, 178

[56] References Cited

U.S. PATENT DOCUMENTS

| | | | |
|---|---|---|---|
| Re. 28,895 | 7/1976 | Noiles | 623/23 |
| 2,719,522 | 10/1955 | Hudack | 623/23 |
| 3,605,123 | 9/1971 | Hahn | 623/18 |
| 3,808,606 | 5/1974 | Tronzo | 623/18 |
| 3,840,904 | 10/1974 | Tronzo | 623/18 |
| 3,943,576 | 3/1976 | Sivash | 623/23 |
| 3,848,272 | 11/1974 | Noiles | 623/263 |
| 4,031,571 | 6/1977 | Heimke et al. | 623/23 |
| 4,068,324 | 1/1978 | Townley et al. | 623/23 |
| 4,206,516 | 6/1980 | Pillar | 623/18 |
| 4,304,011 | 12/1981 | Whelan, III | 623/18 |
| 4,352,212 | 10/1982 | Greene et al. | 623/18 |
| 4,514,865 | 5/1985 | Harris | 623/23 |
| 4,549,319 | 10/1985 | Meyer | 623/23 |

FOREIGN PATENT DOCUMENTS 549 7/1978 European Pat. Off. .
2839661 9/1979 Fed. Rep. of Germany .
83/02555 8/1983 PCT Int'l Appl. .

OTHER PUBLICATIONS

ASTM Standard F370, pp. 79-81, (1973).
Cook et al., *Journal of Biomedical Materials Research*, 18, 497-512, (1984).
Joint Medical Product Corporation's product brochure "SRN Femoral Stem Prosthesis and Collar System" (1983).
Yue et al., *Journal of Biomedical Materials Research*, 18, 1043-1058, (1984).
Zimmer "Implant Metals" product catalog Rev.2A, (Sep., 1974).
Allo Pro product brochure "The Leinbach Horizontal Platform Femoral Component" (cira 1982).
Joint Medical Product Corporation's product brochure entitled "ROM 135 TM Total Hip Prosthesis" (1983).

*Primary Examiner*—Richard J. Apley
*Assistant Examiner*—David J. Isabella
*Attorney, Agent, or Firm*—Maurice M. Klee

[57] ABSTRACT

A joint prosthesis component for implantation in the end of a bone is provided. The component comprises a collar which holds a stem in a fixed position. The envelope of the bone engaging surface of the collar has a shape and size which corresponds to the shape and size of the cancellous bone at the end of the bone in that the envelope of the collar is more ovoid than round, having a larger diameter which lies medially to laterally and a smaller diameter which lies anteriorly to posteriorly when the component is implanted in the end of the bone. In certain preferred embodiments, the collar, but not the stem, is porous coated.

7 Claims, 4 Drawing Sheets

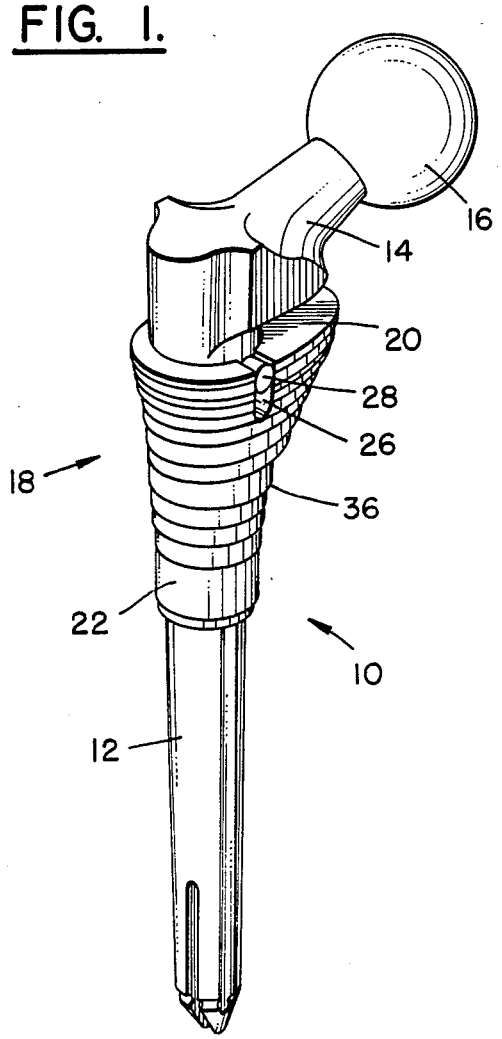
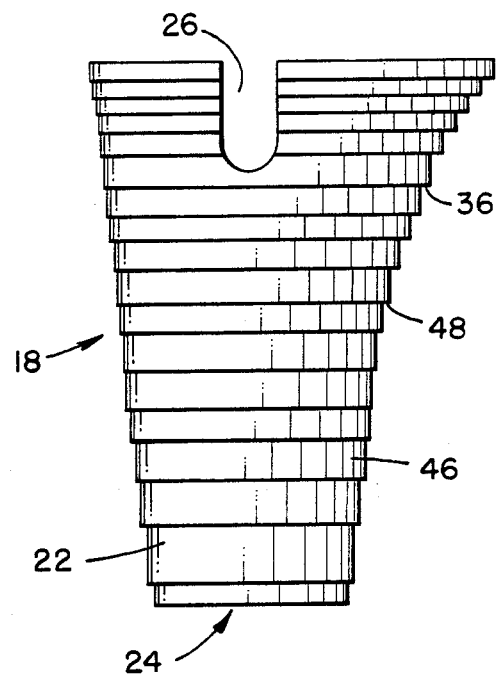
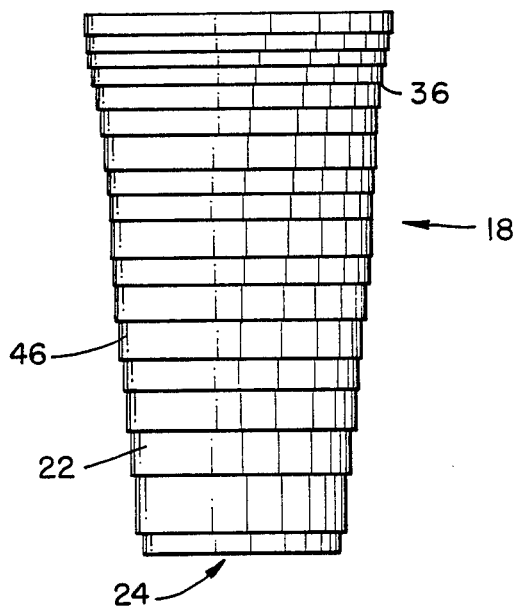
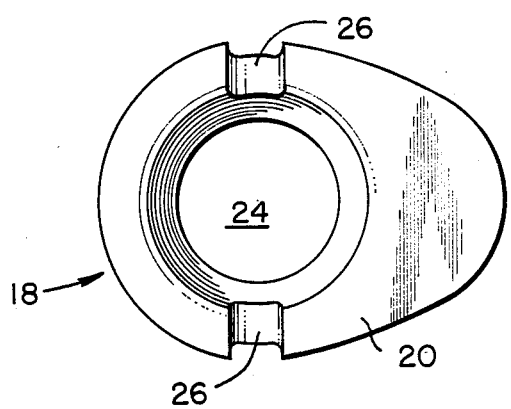
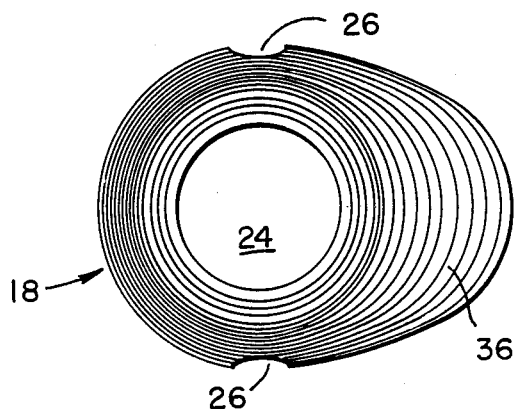

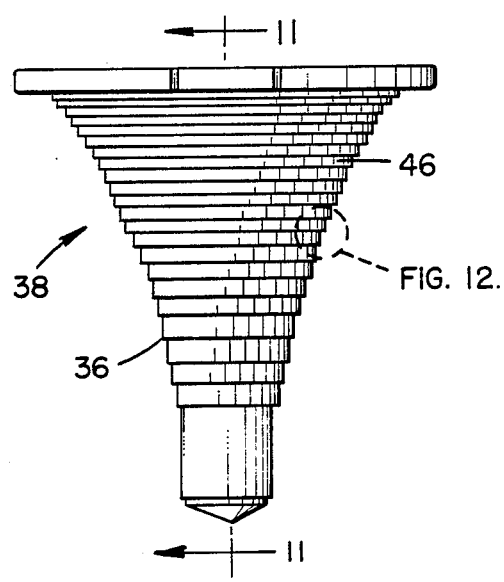
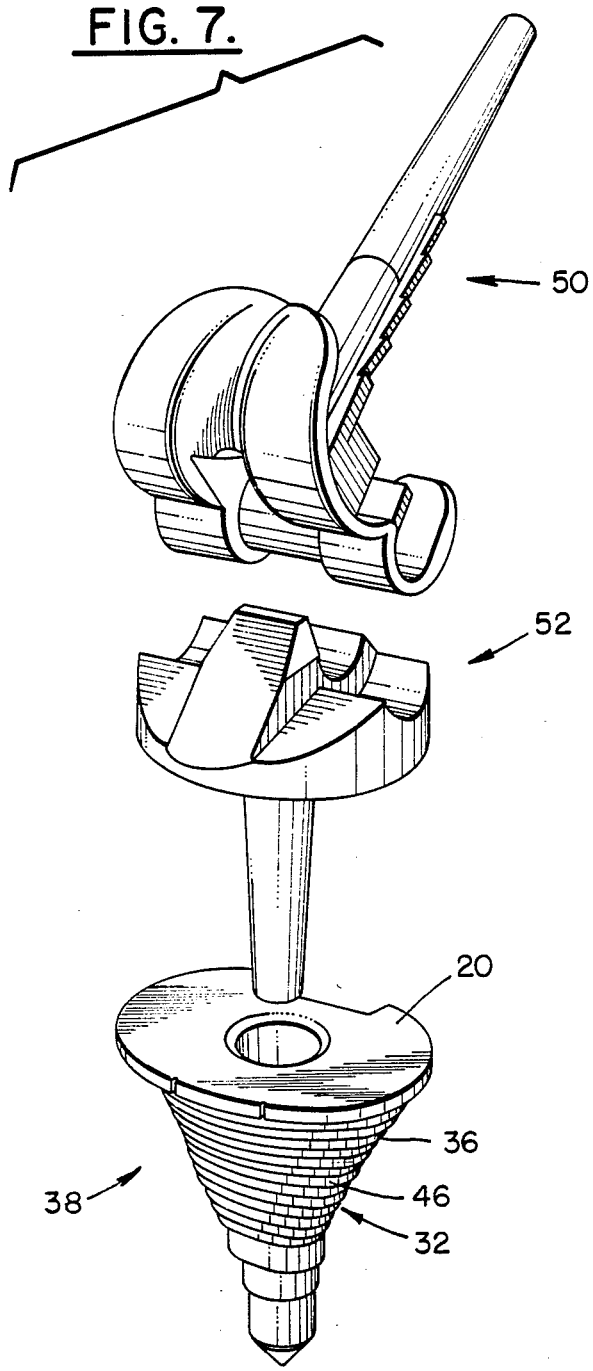
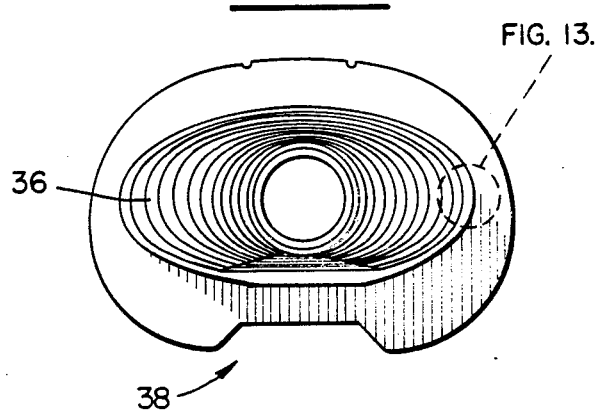
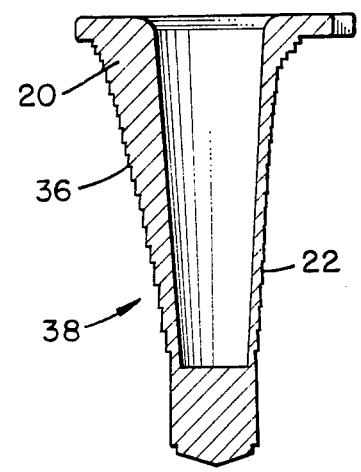
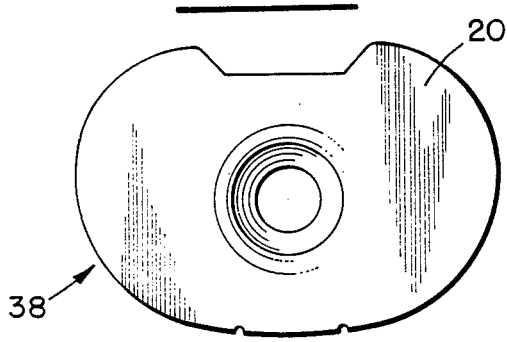

APPARATUS FOR AFFIXING A PROSTHESIS TO BONE

CROSS-REFERENCE TO PRIOR APPLICATIONS

This is a continuation of copending U.S. patent application Ser. No. 011,547, filed Feb. 6, 1987, which is a continuation of U.S. patent application Ser. No. 862,023, filed May 12, 1986, now abandoned, which is a continuation of U.S. patent application Ser. No. 696,270, filed Jan. 30, 1985, now abandoned, which is a continuation of U.S. patent application Ser. No. 578,351, filed Feb. 9, 1984, now abandoned

BACKGROUND OF THE INVENTION

1. Field of the Invention

This invention relates to a method and apparatus for affixing a prosthesis to bone and, in particular, to a method and apparatus for affixing a prosthesis to bone so as to produce stress transfers between the prosthesis and the bone which generally correspond to the stress transfers which occur in natural bone.

2. Description of the Prior Art

The bony portion of human and animal bones consists of two types of tissue: hard or compact bone which is dense in texture, and soft or cancellous bone which consists of fibers and lamellae joined together to form a reticular network. The hard bone makes up the outer wall of the bone and provides most of the bone's overall strength. Cross-sections at all levels through a bone will include some hard bone. The thickness of the hard bone will vary with the level of the cross-section, being smallest near the ends of the bone and greatest at the middle.

Soft bone, where present, forms the inner core of the bone. This type of bone is primarily found near the ends of the bone where the hard bone is thinnest. Current understanding is that, in these regions, the soft bone contributes to the overall strength of the bone by transferring at least some of the applied stresses from the thin portions of the hard bone to relatively large areas of the thicker portions of the hard bone located closer to the middle of the bone. In these regions of stress transfer, the fibers making up soft bone appear to have a regular, equipotential-like, arrangement wherein fibers intersect the hard bone at spaced intervals of approximately 1–2 mm. It is believed that this arrangement, at least in part, is responsible for the efficient transfer of applied stress from one part of hard bone to another.

To date, the methods and apparatus used to attach prostheses to bone have not adequately taken into account the detailed anatomy of bone described above. Specifically, the prior art approaches have failed to provide stress transfer to large areas of the thicker portions of hard bone as occurs in nature through the interaction of soft bone with hard bone. Similarly, the fact that soft bone transfers stress to hard bone at spaced intervals of approximately 1–2 mm has also been ignored.

SUMMARY OF THE INVENTION

In view of the above state of the art, it is an object of the present invention to provide a method and apparatus for attaching a prosthesis to bone wherein stresses are transferred from the prosthesis to the bone in a manner which corresponds to the stress transfers which occur in natural bone. More specifically, it is an object of the invention to provide a method and apparatus for attaching a prosthesis to bone whereby stress is transferred from the prosthesis to relatively large areas of hard bone. It is a further object of the invention to provide a method and apparatus for attaching a prosthesis to bone whereby maximal stress is transferred to hard bone at spaced intervals separated by distances comparable to those at which fibers of soft bone intersect hard bone.

To achieve these and other objects, the invention, in accordance with one of its aspects, provides apparatus for affixing a prosthesis to bone, wherein said bone has an outer wall of hard bone and may have an inner core of soft bone, comprising a body having an outer surface at least a portion of which is contoured to mate with a portion of the inner surface of the hard bone so that, in the region of said mating portions, a substantial fraction of the hard bone is in close proximity to or in contact with the outer surface of the body, said outer surface in said mating region being textured to increase the frictional engagement of the surface with the hard bone.

In accordance with another of its aspects, the invention provides a method for affixing a prosthesis to bone, wherein said bone has an outer wall of hard bone and may have an inner core of soft bone, comprising the steps of:

(a) contouring a portion of the outer surface of the prosthesis to mate with a portion of the inner surface of the hard bone;

(b) providing the contoured portion with a textured surface designed to increase the coefficient of friction between the mating portions of the prosthesis and the hard bone;

(c) reaming some, but not necessarily all, of the soft bone, if present, from the core of the bone; and (d) inserting the prosthesis into the reamed core so as to bring the mating portions of the prosthesis and the hard bone into engagement so that a substantial fraction of the mating portion of the hard bone is in close proximity to or in contact with the mating portion of the prosthesis, and so that, in the region of the mating portions, some of the unreamed soft bone, if present, is crushed between the prosthesis and the hard bone.

In certain preferred embodiments of the invention, the textured surface of the prosthesis is formed from a plurality of spaced, outwardly extending shoulders, the distance between the shoulders being between approximately 0.5 and 5.0 mm so as to generally correspond to the observed spacing between the points of intersection of fibers of soft bone with hard bone.

In other preferred embodiments, the shoulders have sharp outer edges capable of cutting into the inner surface of the hard bone so that as the prosthesis is implanted, portions of the hard bone can be shaved away to produce an increased area of engagement between the prosthesis and the hard bone, while at the same time producing bone chips which will stimulate regenerative bone growth.

In further preferred embodiments, the apparatus is constructed in the form of a hollow collar to which other components of the prosthesis are attached.

In connection with each of these embodiments, parts of the outer surface of the prosthesis can be composed of porous metal into which bone can grow. The use of porous metal is especially preferred with regard to the embodiments in the form of collars because the processes normally used to make metal porous generally weaken the metal and for the collar embodiment this weakening effect can be limited to the collar which typically is subjected to smaller stresses than other parts of the prosthesis.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 1 is a perspective view of the femur portion of an artificial hip joint employing a collar constructed in accordance with the present invention.

FIG. 2 is a side view of the collar of FIG. 1.

FIG. 3 is a top view of the collar of FIG. 1.

FIG. 4 is a bottom view of the collar of FIG. 1.

FIG. 5 is a front view of the collar of FIG. 1.

FIG. 7 is an exploded view of an artificial knee joint employing a tibia sleeve whose outer surface is constructed in accordance with the present invention.

FIG. 8 is a top view of the tibia sleeve of FIG. 7.

FIG. 9 is a front view of the tibia sleeve of FIG. 7.

FIG. 10 is a bottom view of the tibia sleeve of FIG. 7.

FIG. 11 is a cross-sectional view of the tibia sleeve of FIG. 7 along lines 11—11 in FIG. 9.

DESCRIPTION OF THE PREFERRED EMBODIMENTS

Figure 6:
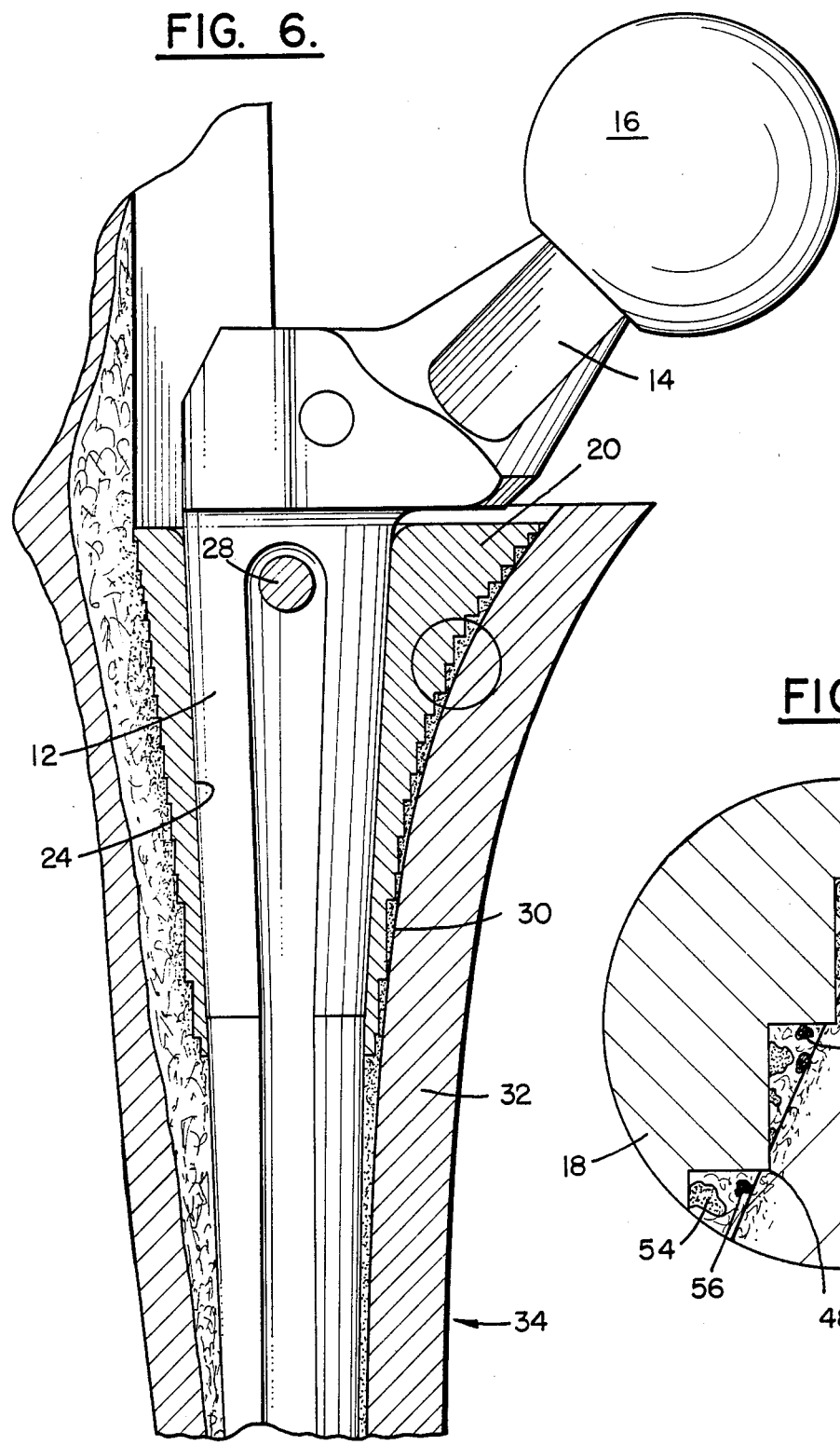
FIG. 6 is a side view partially in section of a femur into which has been implanted the apparatus of FIG. 1.

As discussed above, the present invention relates to a method and apparatus for affixing a prosthesis to bone so as to transfer stresses from the prosthesis to the bone in a manner which generally corresponds to the types of stress transfers which occur in natural bone.

To achieve this result, the prosthesis is provided with an outer surface at least a portion of which is both contoured to mate with a portion of the inner surface of the hard bone to which the prosthesis is being affixed, and provided with a texture which increases the frictional engagement between the outer surface and the hard bone. In this way, applied stresses are effectively transferred from the prosthesis to relatively large areas of hard bone in a manner similar to that which occurs in natural bone through the interaction of soft bone with hard bone. Moreover, by providing the texture with a plurality of spaced regions having high coefficients of friction and by adjusting the spacing between those regions to be on the order of a few millimeters, the anatomical details of the interaction of soft bone with hard bone, wherein fibers of soft bone intersect hard bone every few millimeters, are also approximated.

FIGS. 1-6 and 7-13 illustrate the application of the invention to an artificial hip joint and an artificial knee joint, respectively. It is to be understood that the invention is equally applicable to other artificial joints, including, without limitation, artificial shoulder joints, artificial finger joints, artificial elbow joints, and the like. Along these same lines, in the discussion which appears below, certain features of the invention are described in detail with regard to only one of the two illustrated embodiments, e.g., the artificial hip joint. It is to be understood that these features can be used with both embodiments, as well as with the various other types of artificial joints listed above.

Also, for both the artificial hip joint and the artificial knee joint, the contoured and textured outer surface is shown associated with a separable component of the prosthesis, i.e., collar 18 in FIGS. 1–6 and tibia sleeve 38 in FIGS. 7–13. It is to be understood that this surface need not be carried by a separable component but can form part of the overall outer surface of a unitary prosthetic component, e.g., part of the outer surface of stem 12 in FIGS. 1–6.

Referring specifically to FIG. 1, this figure shows a construction for femur portion 10 of an artificial hip joint. This portion includes a stem 12 to which is attached arm 14 and ball 16. Stem 12, arm 14 and ball 16 can be constructed in a variety of ways known to the art. Particularly preferred constructions for these components are described in U.S. Pat. Nos. 3,820,167, 3,943,576, 3,996,625 and 4,077,070, the pertinent portions of which are included herein by reference.

Femur portion 10 also includes collar 18 which is constructed in accordance with the present invention. Collar 18 includes body 20 having outer surface 22. It also includes walled aperture 24 for receiving stem 12. The walls of aperture 24 taper inwardly from the top to the bottom of collar 18 and mate with a complementary taper on the outside of stem 12. The slopes of these tapers are chosen so that the stem and the collar lock together as the stem is pushed into the collar. To further secure stem 12 to collar 18, the stem is provided with pins 28 which are received in recesses 26 formed in the collar. The pins and recesses prevent rotation of stem 12 within aperture 24.

Figure 6A:
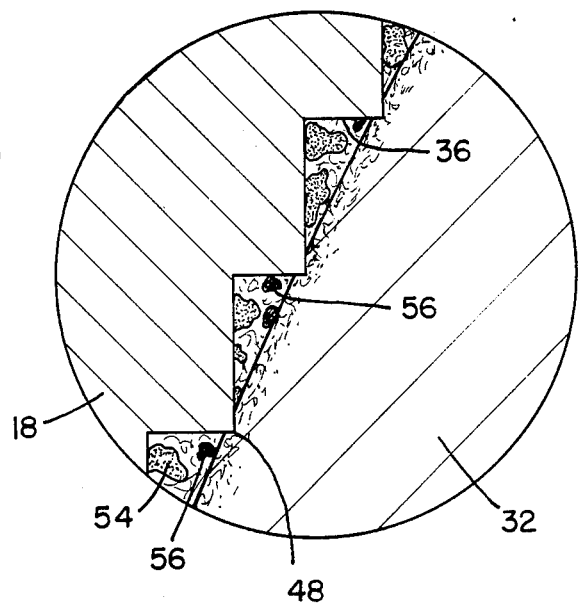
FIG. 6A is an exploded view of the indicated portion of FIG. 6 showing the relationship between the outer surface of the collar and the hard and soft bone of the femur.

As can best be seen in FIGS. 6 and 6A, outer surface 22 of collar 18 is contoured to mate with inner surface 30 of the hard bone portion 32 of bone 34. That is, outer surface 22 is given a shape such that, when collar 18 is implanted in a suitably prepared bone, e.g., the upper part of the femur for a hip prossurface thesis, a substantial fraction of the hard bone's inner surface 30 is in close proximity to or in contact with the prosthesis' outer surface 22.

Because the size and shape of particular human and animal bones varies from individual to individual, to achieve this close fit generally means that the surgeon must be supplied with a family of prostheses having outer surfaces of different sizes and shapes. In this regard, it is preferable to apply the contoured outer surfaces to a small piece, such as collar 18, rather than to a large piece, such as stem 12, since it is substantially less expensive to the manufacturer and much more convenient and economical to the user to provide, store and have available in the operating room a family of small pieces rather than large pieces.

In addition to having a contour which mates with the inner surface of the hard bone into which the prosthesis is to be implanted, outer surface 22 of collar 18 is also provided with a texture which increases the frictional engagement of the surface with the hard bone.

In FIGS. 1-6, the texture comprises a plurality of outwardly extending shoulders 36 oriented to increase the frictional engagement of surface 22 with the hard bone in the direction of the longitudinal axis of bone 34. Similar shoulders are used on tibia sleeve 38 of the artificial knee embodiment shown in FIGS. 7-11.

Figure 12:
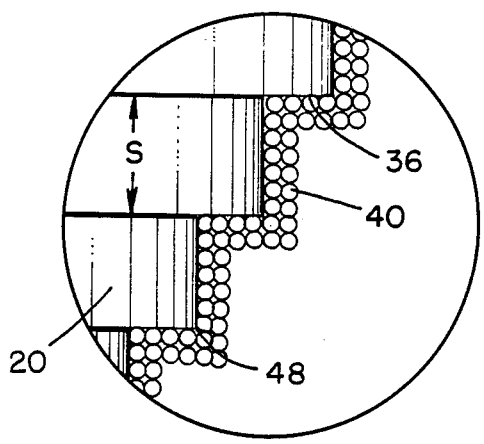
FIGS. 12 and 13 are exploded views of the outer surface of the tibia sleeve of FIG. 7 showing, respectively, a porous coating and a texture designed to increase frictional engagement between the prosthesis and the bone in two directions.

In FIG. 12, in addition to shoulders 36, the outer surface of the prosthesis is provided with a porous surface into which bone can grow. As known in the art, such a surface can be obtained, among other ways, by coating the surface of the component with small balls 40 composed of the same metal as that used to form the component, e.g., a titanium alloy such as one containing 6% aluminum and 4% vanadium (see ASTM Spec. No. F136), and then heating the coated component to fuse the balls and the component together. An appropriate size for the balls relative to the size of the prosthetic component is illustrated in FIG. 12 wherein the distance represented by the longitudinal spacing (S) between shoulders 36 includes on the order of 2-10 balls. As discussed in detail below, this spacing is preferably on the order of between approximately 0.5 and 5.0 mm.

The presence of the porous coating not only allows bone to grow into the prosthesis over time, but, since the roughness of outer surface 22 is increased, also enhances the initial frictional engagement between the prosthesis and the hard bone which occurs at the time of implantation. This initial increase in frictional engagement occurs both in the direction of the longitudinal axis of the bone as well as in the direction corresponding to rotation of the prosthesis about the longitudinal axis of the bone.

Although, in accordance with the invention, porous coatings can be used in combination with a mating contour applied directly to a component which is subjected to high stresses, e.g., stem 12, this approach is believed to entail a risk of failure of the prosthesis with extended periods of use unless the component is substantially redesigned in view of the weakened material. This is so because the heating process used to form the porous coating, as well as the surface characteristics produced by the coating, can significantly reduce the component's fatigue strength.

For some prosthesis materials, e.g., cobalt-chromium alloys, this fatigue strength reduction can be compensated for by formulating or processing the alloy so that it has such a high initial strength that even significant strength reductions do not weaken the component to a point where it will not withstand the stresses associated with long periods of use. However, for other materials, in particular, titanium-containing materials such as the titanium alloy described above, the fatigue problem cannot be overcome by increasing the initial strength of the material. Moreover, for these materials, the reduction in strength caused by porous coating can be as high as 60% or more, e.g., from approximately 90,000 p.s.i. to about 30,000 p.s.i. for the titanium-aluminum-vanadium alloy described above.

In the past, this fatigue strength problem with porous coated, titanium-containing prostheses has been overcome, at least in part, by increasing the cross-sectional dimensions of the prosthesis. Unfortunately, this approach has the significant drawback that to a great extent, it leads to the loss of one of the primary advantages resulting from the use of titanium-containing materials in prostheses, namely, the fact that finished prostheses made from titanium-containing materials have a flexibility closer to that of natural bone than the flexibility achieved with other prosthesis materials, e.g., cobalt-chromium alloys.

In accordance with the present invention, it has now been found that a titanium-containing prosthesis can be porous coated while still maintaining both its overall strength and its flexibility. Specifically, this result is achieved by separating the prosthesis into components, some of which are subjected to relatively high stress, e.g., stem 12, and others of which are subjected to relatively low stress, e.g., collar 18, and then porous coating only the relatively low stress components. In this way, the finished prosthesis can have all three characteristics considered desirable by the art, namely, porous coating, strength, and flexibility.

Figure 13:
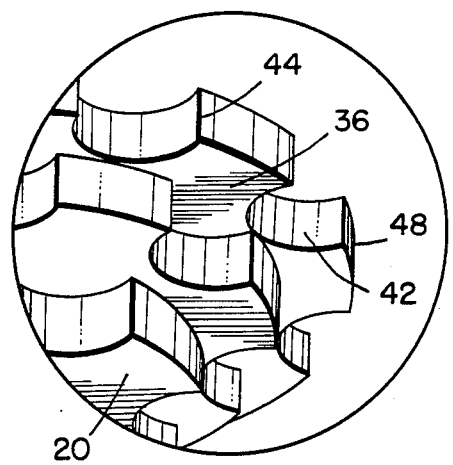

FIG. 13 shows an alternate surface texture designed to increase the frictional engagement of the prosthesis with the hard bone both in the direction of the longitudinal axis of the bone and in direction corresponding to rotation of the prosthesis about the longitudinal axis of the bone. In accordance with this embodiment, cutouts 42 are formed in shoulders 36 so as to produce surface discontinuities 44 which help prevent rotation of the prosthesis about its longitudinal axis. The un-cutout portions of shoulders 36 continue to function as a texture which increases the coefficient of friction between the prosthesis and the bone in the direction of the longitudinal axis of the bone. Most preferably, the spacing between surface discontinuities 44 is on the order of a few millimeters to correspond generally to the spacing observed between the points of intersection of fibers of soft bone with hard bone.

It should be noted that both tibia sleeve 38 and collar 18, as well as the inner surfaces of the hard bone portions of the tibia and femur with which these components mate, have non-circular cross-sections. These cross-sections in and of themselves tend to resist rotation so that in many cases texture enhancement in the direction corresponding to rotation of the prosthesis about the longitudinal axis of the bone may not be required.

As shown in the figures, contoured outer surface 22 of the prosthesis is made up of a plurality of segments 46. Within each segment, the perimeter of the outer surface is constant in both size and shape. Between segments, however, the sizes and/or shapes of the perimeters change so as to produce the contour which mates with the inner surface of the hard bone and so as to provide the shoulders 36 which increase the frictional engagement of the contoured surface with the hard bone.

So that the overall contour of outer surface 22 will be a reasonable approximation of the shape of the inner surface 30 of hard bone 32, or, in other words, so that surfaces 22 and 30 will be in relatively close proximity over a substantial area, it is important to employ a sufficient number of segments 46 so that the outward extent of any shoulder 36 is no greater than approximately 1-2 mm. On the other hand, so that shoulders 36 are effective in increasing the coefficient of friction between the prosthesis and the hard bone, the outward extent of the shoulders should be at least approximately 0.25 mm.

Since the outer edges 48 of shoulders 36 are the regions of outer surface 22 which have the highest coefficients of friction, in order to approximate the manner in which fibers of soft bone intersect with hard bone, the spacing between these edges should be on the order of a few millimeters. Ideally, the spacing should be between approximately 1 and 2 millimeters, but in practice it has been found that to keep the depth of shoulders 36 between approximately 0.25 and 2 mm, it is necessary to use longitudinal spacings between edges 48 which vary between approximately 0.5 and 5.0 mm.

Referring now to FIGS. 7–13, these figures illustrate the application of the invention to an artificial knee joint composed of femur component 50, intermediate bearing member 52 and tibia sleeve 38. A detailed discussion of the construction of this joint can be found in U.S. patent application Ser. No. 578,437, filed on Feb. 9, 1984, now U.S. Pat. No. 4,634,444, to Douglas G. Noiles, entitled "Semi-Constrained Artificial Joint." The pertinent portions of that patent application are incorporated herein by reference.

As discussed above, for the artificial knee joint of FIGS. 7–13, the features of the invention are applied to tibia sleeve 38. Thus this sleeve has a body 20 whose outer surface 22 is contoured to mate with the inner surface of the hard bone at the upper end of the tibia. In addition to being contoured, surface 22 is also textured by means of segments 46 which form spaced shoulders 36. As described in detail above, these shoulders represent regions of increased coefficient of friction between surface 22 and the inside surface of the hard bone. As with the artificial hip embodiment, the combination of a contour which closely matches the shape of the inner surface of the hard bone over a substantial area and the presence of spaced regions having a relatively high coefficient of friction leads to stress transfers between the prosthesis and the hard bone which generally correspond to the stress transfers which occur in natural bone.

Implantation of the prostheses of the present invention follows standard procedures known in the art. Thus, the bone into which the prosthesis is to be inserted is resected as necessary and the core of the bone is reamed of soft bone and marrow. In the region where the contoured surface of the prosthesis and the hard bone will mate, it is desirable to leave some soft bone which can be captured and crushed between the surface and the hard bone as the surface is moved into position. This capturing and crushing process will pulverize some of the soft bone to the point of forming bone chips which can serve as nuclei for regenerative bone growth. The results of the process are illustrated in FIGS. 6 and 6A where the soft bone is identified by the number 54 and bone chips are identified by the number 56.

In addition to capturing and crushing soft bone between the prosthesis and the hard bone, it is also desirable to further generate bone chips from the hard bone. To this end, it is desirable that edges 48 of shoulders 36 be sharp so that they can scrape away parts of the hard bone as the prosthesis is inserted into the bone, and thus automatically form and deposit the desired bone chips at the prosthesis/hard bone interface. In addition to forming bone chips, the use of sharp edges at the ends of shoulders 36 also serves to shave away any high spots on inner surface 30 of hard bone 32 and thus produces an increased area of engagement between the prosthesis and the hard bone.

Although specific embodiments of the invention have been described and illustrated, it is to be understood that modifications can be made without departing from the invention's spirit and scope. For example, surface textures other than those illustrated can be used to enhance the coefficient of friction between the prosthesis and the hard bone. Along these same lines, the contour of the outer surface of the prosthesis need not be formed from discrete segments of the shapes and sizes illustrated, but can be formed from segments having a variety of shapes and sizes or, alternatively, can be formed in a continuous manner without the use of segments with the surface texture being provided separately from contour formation.

What is claimed is:

1. A prosthesis for implantation in an end of a bone, said bone having an inner core of cancellous bone and an outer wall of hard bone, said prosthesis comprising:
   (a) an elongated collar having first and second ends, said collar having a bone engaging outer surface which defines an envelope, the cross section of the envelope in the region of the first end having a larger dimension in a first direction and a smaller dimension in a second direction orthogonal to the first direction so that said cross section is substantially oval; and
   (b) means for holding a stem means carrying a joint motion surface in a fixed position;
   whereby the envelope has a shape and size which generally corresponds to the shape and size of the cancellous bone at the end of the bone in which the prosthesis is implanted.

2. The prosthesis of claim 1 wherein the cross section of the envelope in the region of the second end is substantially round.

3. The prosthesis of claim 1 wherein the bone engaging outer surface of the collar is porous coated.

4. A prosthesis for implantation in an end of a bone, said bone having an inner core of cancellous bone and an outer wall of hard bone, said prosthesis comprising first and second parts wherein:
   (a) the first part includes:
      (i) first means defining a joint motion surface; and
      (ii) a stem which extends into the second part, said stem being attached to said first means; and
   (b) the second part includes:
      (i) means for holding the first part in a fixed position; and
      (ii) an elongated collar having first and second ends, said collar having a bone engaging outer surface which defines an envelope, the cross section of the envelope in the region of the first end having a larger dimension in a first direction and a smaller dimension in a second direction orthogonal to the first direction so that said cross section is substantially oval, whereby the envelope has a shape and size which generally corresponds to the shape and size of the cancellous bone at the end of the bone in which the prosthesis is implanted.

5. The prosthesis of claim 4 wherein the cross section of the envelope in the region of the second end is substantially round.

6. The prosthesis of claim 4 wherein the bone engaging outer surface of the collar is porous coated.

7. The prosthesis of claim 6 wherein the outer surface of said first part is not porous coated.

* * * * *